(12) United States Patent
Li et al.

(10) Patent No.: US 12,115,245 B2
(45) Date of Patent: Oct. 15, 2024

(54) ANTERIOR CHAMBER PERFUSATE FOR INTRAOCULAR SURGERY AND METHOD

(71) Applicant: Xiamen University, Fujian (CN)

(72) Inventors: Cheng Li, Fujian (CN); Mengyi Jin, Fujian (CN); Ying Hong, Fujian (CN); Zuguo Liu, Fujian (CN)

(73) Assignee: Xiamen University, Fujian (CN)

( * ) Notice: Subject to any disclaimer, the term of this patent is extended or adjusted under 35 U.S.C. 154(b) by 643 days.

(21) Appl. No.: 17/461,086

(22) Filed: Aug. 30, 2021

(65) Prior Publication Data

US 2022/0016022 A1    Jan. 20, 2022

Related U.S. Application Data

(63) Continuation of application No. PCT/CN2020/076984, filed on Feb. 27, 2020.

(30) Foreign Application Priority Data

Feb. 28, 2019   (CN) .......................... 201910151759.2

(51) Int. Cl.
| | | |
|---|---|---|
| *A61K 9/00* | (2006.01) | |
| *A61F 9/007* | (2006.01) | |
| *A61K 9/08* | (2006.01) | |
| *A61K 31/198* | (2006.01) | |
| *A61K 47/02* | (2006.01) | |
| *A61K 47/12* | (2006.01) | |

(52) U.S. Cl.
CPC ............ *A61K 9/0048* (2013.01); *A61F 9/007* (2013.01); *A61K 9/08* (2013.01); *A61K 31/198* (2013.01); *A61K 47/02* (2013.01); *A61K 47/12* (2013.01); *A61B 2217/007* (2013.01)

(58) Field of Classification Search
CPC ................................................... A61K 9/0048
See application file for complete search history.

(56) References Cited

FOREIGN PATENT DOCUMENTS

| | | | |
|---|---|---|---|
| CN | 101125149 | A | 2/2008 |
| CN | 103006695 | A | 4/2013 |
| CN | 106420809 | A | 2/2017 |
| CN | 108785251 | A | 11/2018 |
| CN | 109771370 | A | 5/2019 |
| EP | 3357493 | A1 | 8/2018 |
| WO | 2017192584 | A1 | 11/2017 |

OTHER PUBLICATIONS

International Search Report and English Translation cited in PCT/CN2020/076984 mailed May 14, 2020, 6 pages.
Written Opinion cited in PCT/CN2020/076984 mailed May 14, 2020, 4 pages.
Zhang, X. et al. Alanyl-glutamine ameliorates lipopolysaccharide-induced inflammation and barrier function injury in bovine jejunum epithelial cells. Biochem Cell Biol, doi:10.1139/bcb-2018-0320 (2019).33 pages.
Tazuke, et al., "Alanyl-glutamine-supplemented parenteral nutrition prevents intestinal ischemia-reperfusion injury in rats", Journal of Parenteral and Enteral Nutrition, vol. 27, No. 2, 2003, 6 pages.
Carneiro, et al., "Caspase and bid involvement in Clostridium difficile toxin A-induced apoptosis and modulation of toxin A effects by glutamine and alanyl-glutamine in vivo and in vitro", Infection and Immunity, Jan. 2006, p. 81- 87 vol. 74, No. 1.
Hou, et al., "Effects of alanyl-glutamine dipeptide on the expression of colon-inflammatory mediators during the recovery phase of colitis induced by dextran sulfate sodium", Eur J Nutr (2013) 52:1089-1098.
Liu, et al., "Effects of alanyl-glutamine on intestinal adaptation and bacterial translocation in rats after 60% intestinal resection", Clinical Nutrition (1997) 16:75-78.
Nosworthy, et al., "Enterally delivered dipeptides improve small intestinal inflammatory status in a piglet model of intestinal resection", Clinical Nutrition xxx (2015) 1e7, 7 pages.
Calder, P. C. "Glutamine and the immune system", Clmrcal Nurrirron (1994) 13: Z-R, 7 pages.
Li, et al., "Glutamine deprivation alters intestinal tight junctions via a PI3-KAkt mediated pathway in Caco-2 cells", First published online Feb. 11, 2009; doi:10.3945/jn.108.101485., 5 pages.
Stehle, et al., "Isotachophoretic analysis of a synthetic dipeptide I-alanyl-l-glutamine Evidence for stability during heat sterilization", Journal of Chromatography, 294 (1984) 507-512.
Haynes, et al., "L-Glutamine or L-alanyl-L-glutamine prevents oxidant- or endotoxin-induced death of neonatal enterocytes", Amino Acids (2009) 37:131-142.
Araújo Jr., et al., "Preconditioning with L-alanyl-glutamine reduces hepatic ischemia-reperfusion injury in rats", Acta Cirúrgica Brasileira—vol. 26 (Suppl. 1) 2011.
Cavalcante de Vasconcelos, et al., "Preconditioning with L-alanyl-glutamine upon cerebral edema and hypocampus red neurons counting in rats subjected to brain ischemia reperfusion injury", Acta Cirúrgica Brasileira—vol. 30 (3) 2015-199.
Liu, et al., "Protective effects of N(2)-L-alanyl-L-glutamine mediated by the JAK2 STAT3 signaling pathway on myocardial ischemia reperfusion", Molecular Medicine Reports 17: 5102-5108, 2018.

*Primary Examiner* — Golam M Shameem
(74) *Attorney, Agent, or Firm* — Cooper Legal Group, LLC

(57) ABSTRACT

An anterior chamber perfusate for intraocular surgery and its use. The anterior chamber perfusate not only balances intraocular pressure, but also contains a certain amount of L-alanyl-L-glutamine (Ala-Gln).

8 Claims, 1 Drawing Sheet

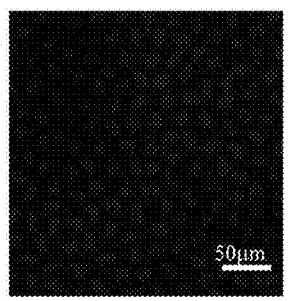
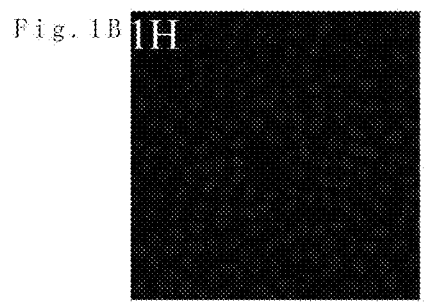
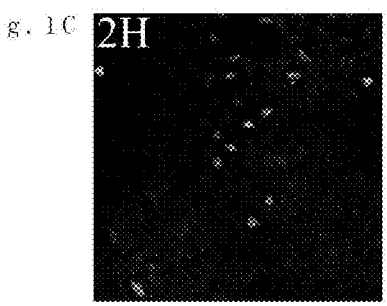
Fig.1A    Fig.1B    Fig.1C
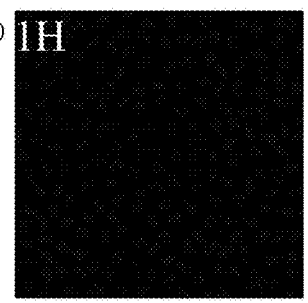
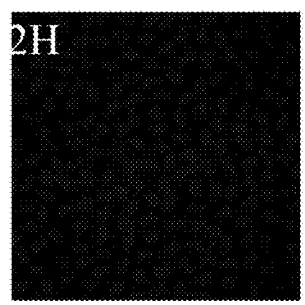
Fig.1D    Fig.1E
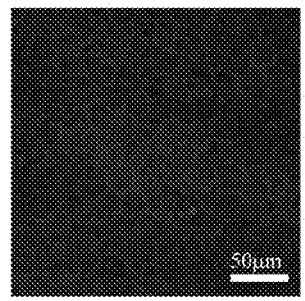
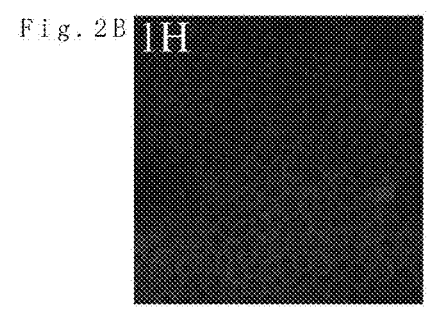
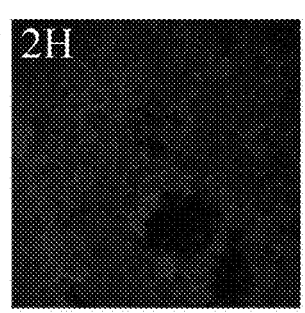
Fig.2A    Fig.2B    Fig.2C
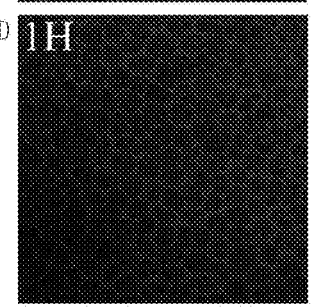
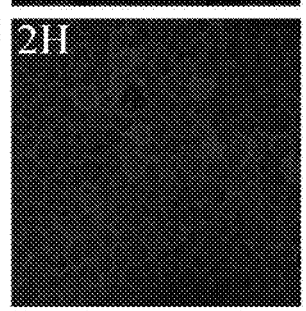
Fig.2D    Fig.2E
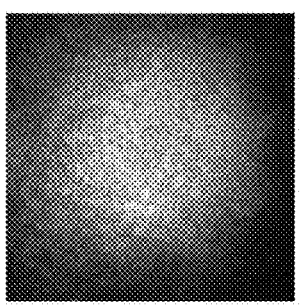
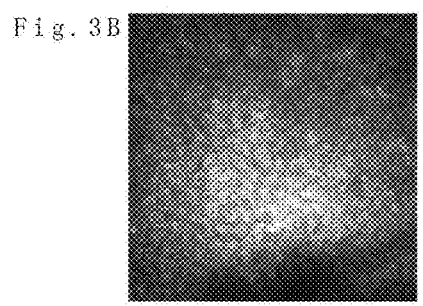
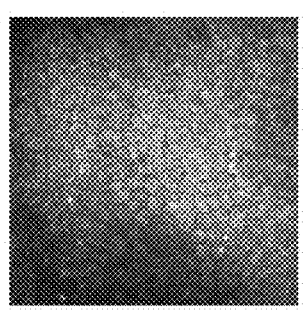
Fig.3A    Fig.3B    Fig.3C

ANTERIOR CHAMBER PERFUSATE FOR INTRAOCULAR SURGERY AND METHOD

RELATED APPLICATIONS

This application is a continuation of International patent application PCT/CN2020/076984, filed on Feb. 27, 2020, which claims priority to Chinese patent application 201910151759.2, filed on Feb. 28, 2019. International patent application PCT/CN2020/076984 and Chinese patent application 201910151759.2 are incorporated herein by reference.

FIELD OF THE DISCLOSURE

The present disclosure relates to medication, and in particular relates to an anterior chamber perfusate for intraocular surgery and a method.

BACKGROUND OF THE DISCLOSURE

With the development of microscope technology, internal eye surgery has become more mature, and the number of surgeries has increased year by year. The surgery rescues many blind patients. Intraocular surgeries, such as extracapsular cataract extraction, intraocular lens implantation, and vitrectomy, require a long period of solution perfusion in order to balance the intraocular pressure. The conventional intraocular perfusate is an ophthalmic balanced salt solution, which lacks nutrients and antioxidant effects. During a long surgery, long-term contact with corneal endothelial cells by the solution can easily cause cell inactivation or even large areas of apoptosis and shedding (i.e., the conventional intraocular perfusate inevitably affects the corneal endothelial cells). The vision recovery of patients after transplantation is closely related to the activity of corneal endothelial cells. Glutamine (Gln) is the most abundant free amino acid in the body, accounting for about 60% of the total free amino acids in the human body, and Gln is also the nitrogen source for many biosynthetic pathways. Gln is essential for regulating the integrity of tight junction proteins and intercellular connections between intestinal cells in parenteral nutrition, and can effectively protect the intestinal barrier function. However, Gln is unstable during storage and heat sterilization and has low solubility in aqueous solutions, which limits the range of applications for Gln. L-alanyl-L-glutamine (Ala-Gln), also known as glutathione, is an amino acid chemical agent that can release glutamine into the body. It is currently mainly used for parenteral and enteral nutrition supplementation, and the protection of tissue and organ ischemia-reperfusion injury after surgery. There is no report on the application of anterior chamber perfusion solution in intraocular surgery.

1 Calder, P. C. Glutamine and the immune system. *Clin Nutr* 13, 2-8 (1994).
2 Li, N. & Neu, J. Glutamine deprivation alters intestinal tight junctions via a PI3-K/Akt mediated pathway in Caco-2 cells. *J Nutr* 139, 710-714, doi:10.3945/jn.108.101485 (2009).
3 Stehle P, P. P., Furst P Isotachophoretic analysis of a synthetic dipeptide L-alanyl-glutamine evidence for stability during heat sterilization *Journal of Chromatography* 294, 507-512 (1984).
4 Liu, S., Yang, Y., Song, Y. Q., Geng, J. & Chen, Q. L. Protective effects of N(2)LalanylLglutamine mediated by the JAK2/STAT3 signaling pathway on myocardial ischemia reperfusion. *Mol Med Rep* 17, 5102-5108, doi:10.3892/mmr.2018.8543 (2018).
5 Tazuke, Y., Wasa, M., Shimizu, Y., Wang, H. S. & Okada, A. Alanyl-glutamine-supplemented parenteral nutrition prevents intestinal ischemia-reperfusion injury in rats. *JPEN J Parenter Enteral Nutr* 27, 110-115, doi:10.1177/0148607103027002110 (2003).
6 Araujo Junior, R. J. et al. Preconditioning with L-alanyl-glutamine reduces hepatic ischemia-reperfusion injury in rats. *Acta Cir Bras* 26 Suppl 1, 8-13 (2011).
7 Vasconcelos, P. R., Guimaraes, A. B., Campelo, M. W., Vasconcelos, P. R. & Guimaraes, S. B. Preconditioning with L-alanyl-glutamine upon cerebral edema and hypocampus red neurons counting in rats subjected to brain ischemia/reperfusion injury. *Acta Cir Bras* 30, 199-203, doi:10.1590/50102-865020150030000006 (2015).
8 Liu, Y. W., Bai, M. X., Ma, Y. X. & Jiang, Z. M. Effects of alanyl-glutamine on intestinal adaptation and bacterial translocation in rats after 60% intestinal resection. *Clin Nutr* 16, 75-78 (1997).
9 Zhang, X. et al. Alanyl-glutamine ameliorates lipopolysaccharide-induced inflammation and barrier function injury in bovine jejunum epithelial cells. *Biochem Cell Biol*, doi:10.1139/bcb-2018-0320 (2019).
10 Carneiro, B. A. et al. Caspase and bid involvement in *Clostridium difficile* toxin A-induced apoptosis and modulation of toxin A effects by glutamine and alanyl-glutamine in vivo and in vitro. *Infect Immun* 74, 81-87, doi:10.1128/IAI.74.1.81-87.2006 (2006).
11 Hou, Y. C., Chu, C. C., Ko, T. L., Yeh, C. L. & Yeh, S. L. Effects of alanyl-glutamine dipeptide on the expression of colon-inflammatory mediators during the recovery phase of colitis induced by dextran sulfate sodium. *Eur J Nutr* 52, 1089-1098, doi:10.1007/s00394-012-0416-3 (2013).
12 Haynes, T. E. et al. L-Glutamine or L-alanyl-L-glutamine prevents oxidant- or endotoxin-induced death of neonatal enterocytes. *Amino Acids* 37, 131-142, doi:10.1007/s00726-009-0243-x (2009).
13 Nosworthy, M. G., Dodge, M. E., Bertolo, R. F. & Brunton, J. A. Enterally delivered dipeptides improve small intestinal inflammatory status in a piglet model of intestinal resection. *Clin Nutr* 35, 852-858, doi:10.1016/j.clnu.2015.05.013 (2016).

BRIEF SUMMARY OF THE DISCLOSURE

In order to overcome the deficiencies of the existing techniques, an objective of the present disclosure is to provide an anterior chamber perfusate for intraocular surgery and its method. The anterior chamber perfusate not only balances intraocular pressure, but also contains a certain amount of L-alanyl-L-glutamine (Ala-Gln) to solve the deficiencies of glutamine, namely that glutamine has unstable characteristics and low solubility. The anterior chamber perfusate for intraocular surgery not only protects the corneal endothelial cells from intraoperative mechanical damage, ischemia, and hypoxia of the corneal endothelial cells, but also provides nutrients and is used for intraoperative perfusion. When the anterior chamber perfusate acts on corneal endothelial cells, the anterior chamber perfusate preventively reverses apoptosis and exfoliation of corneal endothelial cells and protects the barrier function of the corneal endothelium, thus better surgical effects are achieved.

In order to solve the technical problems, a first solution of the present disclosure is as follows.

An anterior chamber perfusate for intraocular surgery, the anterior chamber perfusate is an ophthalmic balanced salt solution comprising 0.217-1.090 mg/mL L-alanyl-L-glutamine.

In an embodiment, the ophthalmic balanced salt solution comprises 1.085-1.087 mg/mL of L-alanyl-L-glutamine.

In an embodiment, the ophthalmic balanced salt solution comprises 5.95-6.00 mg/mL sodium chloride, 0.29-0.30 mg/mL potassium chloride, 0.19-0.20 mg/mL calcium chloride, and 3.05-3.15 mg/mL sodium lactate.

In order to solve the technical problems, a second solution of the present disclosure is as follows.

A method for applying the anterior chamber perfusate for intraocular surgery.

A molecular structure of L-alanyl-L-glutamine is follows.

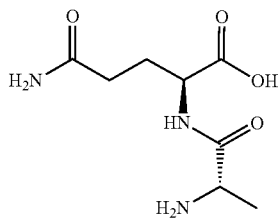

Ala-Gln has a stable characteristic, is soluble in water, and can resist a high temperature sterilization. Ala-Gln can be quickly decomposed to release glutamine (Gln) to play a role in vivo. Bioavailability is high, an application range is wide, insufficiency of Gln is supplemented, and Ala-Gln plays an important role for sudden trauma patient and is a drug in parenteral nutrition guidelines. The anterior chamber perfusate for intraocular surgery of the present disclosure balances intraocular pressure and further contains a certain amount of Ala-Gln. As a synthetic dipeptide of Gln, Ala-Gln is stable after heat sterilization and is very soluble in water. Studies have shown that Ala-Gln can prevent ischemia-reperfusion injuries of cardiac muscle, intestine, liver, or brain. In addition, Ala-Gln can increase an expression of tight junction protein in parenteral nutrition and maintain a thickness of intestinal mucosa and a height of villi to maintain intestinal barrier function. In addition, Ala-Gln can further inhibit a release of inflammatory factors in different physiological environments, reduce inflammation, promote cell proliferation, and prevent cell apoptosis and oxidative damage. The anterior chamber perfusate for intraocular surgery of the present disclosure is used for intraoperative perfusion (i.e., intraoperative anterior chamber perfusion). The anterior chamber perfusate not only protects against intraoperative mechanical damage, ischemia, and hypoxia of the corneal endothelial cells, but also provides nutrients, protects cells from surgical stress, improves anti-oxidation and anti-apoptosis ability of the cells, preventively reverses apoptosis and exfoliation of corneal endothelial cells, and protects the barrier function of the corneal endothelium, and thus better surgical effects are achieved.

BRIEF DESCRIPTION OF THE DRAWINGS

The present disclosure will be further described in combination with the accompanying embodiments and drawings.

FIGS. 1A-1E illustrate photographs of apoptosis of corneal endothelial cells of all experimental groups and control groups in vitro detected by a TdT-mediated dUTP Nick-End Labeling (TUNEL) method. FIG. 1A illustrates a normal group in vitro; FIG. 1B illustrates a control group treated for 1 hour; FIG. 1C illustrates a control group treated for 2 hours; FIG. 1D illustrates an experimental group treated for 1 hour; and FIG. 1E illustrates an experiment group treated for 2 hours.

FIGS. 2A-2E illustrate photographs of F-actin of corneal endothelial cytoskeleton of all experimental groups and control groups in vitro detected by an immunofluorescence staining method. FIG. 2A illustrates a normal group in vitro; FIG. 2B illustrates a control group treated for 1 hour; FIG. 2C illustrates a control group treated for 2 hours; FIG. 2D illustrates an experimental group treated for 1 hour; and FIG. 2E illustrates an experiment group treated for 2 hours.

FIGS. 3A-3C illustrate morphologies of corneal endothelial cells after anterior chamber perfusion detected by in vivo confocal microscopy. FIG. 3A illustrates a normal group; FIG. 3B illustrates a control group treated for 1 hour; and FIG. 3C illustrates an experimental group treated for 1 hour.

DETAILED DESCRIPTION OF THE EMBODIMENTS

The present disclosure will be further described using the accompanying embodiments.

Embodiment 1: Preparation of Anterior Chamber Perfusate for Intraocular Surgery

The anterior chamber perfusate for intraocular surgery in this embodiment comprises the following components per 1 mL:

Sodium chloride 5.95-6.00 mg,
Potassium chloride 0.29-0.30 mg,
Calcium chloride 0.19-0.20 mg,
Sodium lactate 3.05-3.15 mg, and
L-alanyl-L-glutamine 0.217-1.086 mg.

Embodiment 2: Processing Corneal Experiment and Anterior Chamber Perfusion Experiment Using the Anterior Chamber Perfusate I. Subjects 30 healthy and clean ICR mice aged 6-8 weeks, weighing 20-25 g, and including male or female.

II. Experimental Reagents

L-alanyl-L-glutamine, Invitrogen™ Alexa Fluor™ 594 Phalloidin, Triton X-100, bovine Serum Albumin (BSA), phosphate buffer solution (PBS), pentobarbitone, acetone, compound tropicamide eye drops, and 4',6-diamidino-2-phenylindole (DAPI) staining fluid.

III. Experimental Equipment

Operating microscope, a laser confocal scanning microscope (Olympus FV1000MPE-B, Olympus), and Heidelberg Retinal Tomography (HRT3).

IV. Experimental Method

1. Separating Cornea

The ICR mice were sacrificed by a cervical dislocation method, and eyeballs were taken off. After the eyeballs were washed by normal saline, mouse cornea was cut along corneal limbi, and irises, ciliary bodies, etc. were removed. The cornea was separated under the operating microscope to prevent the cornea from mechanical damage.

2. Processing the Cornea 2.1 In Vitro Experimental Group

The cornea was quickly added into a container containing the anterior chamber perfusate obtained in Embodiment 1. The time at which the cornea was added into the container was defined as 0 o'clock. The cornea was taken out after 1 hour or 2 hours and was fixed by 4% paraformaldehyde at 4° C. overnight. Cell apoptosis was detected by a TUNEL method, and F-actin was stained to detect corneal endothelial cytoskeleton by an immunofluorescence staining method.

2.2 In Vitro Control Group

The cornea was separated according to the aforementioned steps, and the cornea was quickly added into a conventional perfusate (e.g., ophthalmic balanced salt solution, that is, L-alanyl-L-glutamine was not added, components and contents of the rest of the elements of the conventional perfusate are the same as the anterior chamber perfusate for intraocular surgery of Embodiment 1). The time at which the cornea was added into the conventional perfusate was defined as 0 o'clock. The cornea was taken out after 1 hour or 2 hours and was fixed by 4% paraformaldehyde at 4° C. overnight. Cell apoptosis was detected by the TUNEL method, and the F-actin was stained to detect the corneal endothelial cytoskeleton by the immunofluorescence staining method.

2.3 In Vitro Normal Group

The cornea was separated according to the aforementioned steps and was fixed by 4% paraformaldehyde at 4° C. overnight without any additional treatment. Cell apoptosis was detected by the TUNEL method, and the F-actin was stained to detect the corneal endothelial cytoskeleton by the immunofluorescence staining method.

3. Anterior Chamber Perfusion

The mice were anesthetized by 5 mL/kg of 1% pentobarbital. At room temperature (i.e. 20-30° C.), compound tropikamide eye drops were used to dilate pupils, and eyelids were opened by lid openers. At the 4 o'clock position of the corneal limbi, a 32 G needle was used to puncture the anterior chamber at a position 2 mm away from the limbi at a 15° angle, and a 34 G metal perfusion needle was inserted and was fixed to prevent the 34 G metal perfusion needle from contacting the corneal endothelium layer and the iris surface.

3.1 In Vivo Experimental Group

The perfusion needle was quickly connected to the anterior chamber perfusate obtained in Embodiment 1, and the anterior chamber was perfused at a constant flow rate of 10 drops per minute. The time at which the anterior chamber was perfused was defined as 0 o'clock. The perfusion was stopped after 1 hour, and a photo of corneal endothelial cells was immediately taken by in vivo confocal microscopy.

3.2 In Vivo Control Group

The perfusion needle was immediately connected to the conventional perfusate, and the anterior chamber was perfused at the same flow rate. The time at which the anterior chamber was perfused was defined as 0 o'clock. The perfusion was stopped after 1 hour, and a photo of corneal endothelial cells was immediately taken by in vivo confocal microscopy.

3.3 In Vivo Normal Group

A photo of corneal endothelial cells was taken by in vivo confocal microscopy without any perfusion treatment.

4. Cell Apoptosis was Detected by the TUNEL Method

The cornea obtained in the aforementioned steps was placed in a 1.5 mL centrifuge tube with the corneal endothelial cells facing upward and was washed by 1×PBS, and was then fixed by cold acetone for 3 minutes. The cornea was washed with 1×PBS and was then permeated by 1% TD-Buffer at room temperature (i.e. 20-30° C.) 3 times for 10 minutes each time. After the cornea was washed by 1×PBS, incubated with Equilibration Buffer at 4° C. for 1 hour, the cornea was then incubated with the rTDT solution prepared in a kit at 4° C. for 4 hours, incubated with 2× saline-sodium citrate (SSC) solution at 4° C. for 40 minutes in the dark to terminate the reaction, washed by 1×PBS, and mounted by DAPI.

5. Immunofluorescence Staining of a Flat Tile of a Full Corneal

The cornea obtained in the aforementioned steps was placed in a 1.5 mL centrifuge tube containing 4% paraformaldehyde with the corneal endothelial cells facing upward and was processed at 4° C. overnight. The cornea was washed by 1×PBS and was then fixed by cold acetone for 3 minutes. The cornea was washed by 1×PBS and was then permeated by 1% TD—Buffer 3 times for 10 minutes each time. The cornea was placed into 2% BSA solution and was blocked for 1 hour at room temperature. With respect to phalloidin staining, the blocked cornea was incubated with F-actin (1:150) staining solution for 90 minutes at room temperature. The cornea was washed with 1×PBS, then mounted by DAPI, and then scanned and recorded by the laser confocal microscope.

V. Experimental Results

1. Cell Apoptosis was Detect by the TUNEL Method

Referring to FIG. 1, nuclei of apoptotic corneal endothelial cells were stained green under the laser confocal microscope, and nuclei of normal corneal endothelial cells turned blue. The experimental group and the control group comprised only a small number of apoptotic cells at 1 hour. When experimental time prolonged to 2 hours, a large number of apoptotic cell nuclei were observed in the corneal endothelial cells of the control group, and only a small amount of fluorescence was observed in the experimental group.

2. Immunofluorescence Staining to Detect Cytoskeleton

Referring to FIG. 2A, under the laser confocal microscope, the normal corneal endothelial cells were regularly and tightly arranged, and the corneal endothelial cytoskeletons had regular double-track-like structures. At 1 hour, the control group exhibited scattered loss of the corneal endothelial cells, the experimental group comprised full corneal endothelium, and an arrangement of the corneal endothelial cytoskeletons in the experimental group was regular. When the experiment was prolonged to 2 hours, the corneal endothelial cytoskeletons were rearranged in the control group, a large number of the corneal endothelial cells fell off, and an integrity and barrier function of the corneal endothelium were destroyed. The corneal endothelial cytoskeletons of the experimental group did not change significantly after 2 hours.

3. Results of the In Vivo Confocal Microscopy

Referring to FIG. 3, the corneal endothelial cells of the normal group were hexagonal, sizes were equal, and intercellular connections were tight. In the experimental group, after the anterior chamber was perfused, pleomorphism of the corneal endothelial cells increased, cell boundaries were clear, no exfoliation of the corneal endothelial cells were observed, and the intercellular connections were complete. In the control group, after the anterior chamber was perfused, the corneal endothelial cells lost their normal hexagonal shapes, intercellular spaces were enlarged, borders were unclear, and nuclei were highly light-reflective.

The intraocular perfusate of the present disclosure not only maintained original perfusion and balances intraocular pressure, but had no toxicity or side effects on intraocular tissues. A certain concentration of Ala-Gln was added to protect from intraoperative ischemia and hypoxia, to provide nutrients, to prevent from apoptosis and exfoliation of the corneal endothelial cells, to maintain morphologies of corneal endothelial cells, to protect integrity and barrier function of the corneal endothelium, and to obtain better surgical results. Thus a good and new anterior chamber perfusate for intraocular surgery was provided.

The aforementioned embodiments are merely some embodiments of the present disclosure, and the scope of the disclosure is not limited thereto. Thus, it is intended that the present disclosure cover any modifications and variations of the presently presented embodiments provided they are made without departing from the appended claims and the specification of the present disclosure.

What is claimed is:

1. An anterior chamber perfusate for intraocular surgery, wherein the anterior chamber perfusate is an ophthalmic balanced salt solution comprising 0.217-1.090 mg/mL L-alanyl-L-glutamine.

2. The anterior chamber perfusate for intraocular surgery according to claim 1, wherein the ophthalmic balanced salt solution comprises 1.085-1.087 mg/mL of L-alanyl-L-glutamine.

3. The anterior chamber perfusate for intraocular surgery according to claim 1, wherein the ophthalmic balanced salt solution comprises 5.95-6.00 mg/mL sodium chloride, 0.29-0.30 mg/mL potassium chloride, 0.19-0.20 mg/mL calcium chloride, and 3.05-3.15 mg/mL sodium lactate.

4. The anterior chamber perfusate for intraocular surgery according to claim 2, wherein the ophthalmic balanced salt solution comprises 5.95-6.00 mg/mL sodium chloride, 0.29-0.30 mg/mL potassium chloride, 0.19-0.20 mg/mL calcium chloride, and 3.05-3.15 mg/mL sodium lactate.

5. A method for applying the anterior chamber perfusate for intraocular surgery according to claim 1.

6. A method for applying the anterior chamber perfusate for intraocular surgery according to claim 2.

7. A method for applying the anterior chamber perfusate for intraocular surgery according to claim 3.

8. A method for applying the anterior chamber perfusate for intraocular surgery according to claim 4.

* * * * *